(12) United States Patent
Benner et al.

(10) Patent No.: US 12,145,145 B2
(45) Date of Patent: Nov. 19, 2024

(54) LABORATORY WELL PLATE WASHING DEVICE AND ASSOCIATED METHOD

(71) Applicant: GRENOVA, INC., Richmond, VA (US)

(72) Inventors: Nolan Benner, Richmond, VA (US); Ali Safavi, Richmond, VA (US); Taylor Anderson, Henrico, VA (US); John Crawford Turner, III, Henrico, VA (US); Brennan Chaloux, Henrico, VA (US); Raphael Santore, Richmond, VA (US)

(73) Assignee: GRENOVA, INC., Richmond, VA (US)

( * ) Notice: Subject to any disclaimer, the term of this patent is extended or adjusted under 35 U.S.C. 154(b) by 41 days.

(21) Appl. No.: 17/901,809

(22) Filed: Sep. 1, 2022

(65) Prior Publication Data
US 2023/0072202 A1 Mar. 9, 2023

Related U.S. Application Data

(60) Provisional application No. 63/241,133, filed on Sep. 7, 2021.

(51) Int. Cl.
*B08B 9/032* (2006.01)
*A61L 2/10* (2006.01)
(Continued)

(52) U.S. Cl.
CPC ............... *B01L 13/02* (2019.08); *A61L 2/10* (2013.01); *A61L 2/26* (2013.01); *B08B 3/022* (2013.01);
(Continued)

(58) Field of Classification Search
CPC ................................ B01L 13/02; B08B 9/0323
See application file for complete search history.

(56) References Cited

U.S. PATENT DOCUMENTS 6,112,603 A * 9/2000 Pietila ................... B01L 3/0203
73/863.23
7,516,749 B2 4/2009 Felder et al.
(Continued)

FOREIGN PATENT DOCUMENTS

DE 4128698 A1 3/1993

OTHER PUBLICATIONS

PurePLATE MCS, IonField Systems, available at https://ionfieldsystems.com/products/pureplate-mcs/, last accessed Aug. 25, 2022, 6 pages.
(Continued)

*Primary Examiner* — Natasha N Campbell
(74) *Attorney, Agent, or Firm* — Welsh Flaxman & Gitler LLC

(57) ABSTRACT

A device for cleaning items comprises an enclosure defining a wash chamber, a rotor positioned within the wash chamber and selectively rotatable about an axle, a motor for selectively rotating the axle, a dispenser, and a drain. The rotor comprises a plurality of holders spaced about the axle and adapted to selectively receive and hold a respective item to be cleaned. The dispenser at least one liquid input and at least one liquid output and is positioned such that the at least one liquid output directs cleaning fluid at one of the items to clean material out of the cavities. The drain is for draining the cleaning fluid out of the chamber. The rotor is selectively rotatable at a predefined rotational speed for a predefined amount of time to expel cleaning fluid from the cavities of each item to be cleaned.

9 Claims, 11 Drawing Sheets

(51) Int. Cl.
*A61L 2/26* (2006.01)
*B08B 3/02* (2006.01)
*B08B 3/12* (2006.01)

(52) U.S. Cl.
CPC ............ *B08B 3/123* (2013.01); *B08B 9/0323* (2013.01); *A61L 2202/11* (2013.01); *A61L 2202/20* (2013.01); *B08B 2209/032* (2013.01)

(56) References Cited

U.S. PATENT DOCUMENTS

| | | | |
|---|---|---|---|
| 10,338,063 | B2 | 7/2019 | Wang et al. |
| 10,961,997 | B2 | 3/2021 | Many et al. |
| 2008/0318755 | A1 | 12/2008 | Yamada |
| 2010/0294319 | A1* | 11/2010 | Massaro ............... B08B 3/02 134/52 |
| 2012/0227774 | A1 | 9/2012 | Pongolini |
| 2012/0279611 | A1 | 11/2012 | Drenguls |
| 2016/0157696 | A1* | 6/2016 | Safavi ............... A61L 2/10 134/22.12 |
| 2016/0187330 | A1* | 6/2016 | Wang ............... B08B 3/06 506/3 |
| 2019/0022670 | A1 | 1/2019 | Mann et al. |
| 2019/0145968 | A1 | 5/2019 | Wang et al. |
| 2019/0170740 | A1 | 6/2019 | Wang et al. |
| 2021/0138485 | A1* | 5/2021 | Mann ............... B04B 7/04 |
| 2021/0301811 | A1 | 9/2021 | Many et al. |

OTHER PUBLICATIONS

Squirt Microplate Washer by Matrical, Inc., SelectScience, available at https://www.selectscience.net/products/squirt-microplate-washer/?prodID=85115#tab-2, last accessed Aug. 25, 2022, 4 pages.
EL406 Washer Dispenser, Agilent Technologies, available at https://www.biotek.com/products/liquid-handling-combination-microplate-washer-dispenser/el406-washer-dispenser/, last accessed Aug. 25, 2022, 8 pages.
Brochure for C.WASH Non-Contact Plate Washer by Cytena, last accessed Sep. 1, 2022, 8 pages.

* cited by examiner

LABORATORY WELL PLATE WASHING DEVICE AND ASSOCIATED METHOD

CROSS-REFERENCE TO RELATED APPLICATIONS

This application claims priority to U.S. Provisional Application Ser. No. 63/241,133, filed Sep. 7, 2021, the contents of which are incorporated herein by reference in its entirety.

FIELD OF THE INVENTION

This invention relates to laboratory consumables, and more particularly to a device and method for washing laboratory consumables.

BACKGROUND

Laboratory consumables are items that are used once in a laboratory and then discarded. As an example, every year around 4,000,000 pounds of plastic pipette tips, after a single use, are disposed of in landfills globally, leading to significant environmental pollution and costs. A typical laboratory consumes several thousand pipette tips daily for samples and assay procedures. Due to the lack of options for cleaning plastic consumables, the labs discard pipette tips after each use. Such high consumption of plastic tips adds $25,000-$1.5M to the annual operation cost to each of the approximately 14,000 research laboratories in the US.

Devices that are capable of efficient pipette tip cleaning and sanitization could save businesses substantial amounts of money in their scientific operations and drastically reduce the amount of waste produced in the course of operations. Devices and methods for cleaning and drying pipette tips have been developed by the applicant of the present invention. Such devices and methods are disclosed in the following co-owned patents, which are incorporated by reference in their entireties: U.S. Pat. No. 9,421,289, issued Aug. 23, 2016; U.S. Pat. No. 10,155,055, issued Dec. 18, 2018; U.S. Pat. No. 10,576,175, issued Mar. 3, 2020; U.S. Pat. No. 9,744,570, issued Aug. 29, 2017; U.S. Pat. No. 10,285,564, issued May 14, 2019; and U.S. Pat. No. 10,024,599, issued Jul. 17, 2017.

Another example of laboratory consumables that are used and disposed of in large numbers is laboratory well plates. A well plate (which may also be termed a microplate, a Microtiter™ plate, a microwell plate, or a multiwell plate) is a flat plate with multiple "cavities" or cavities that are used as small test tubes. Well plates are used extensively in analytical research and clinical diagnostic testing laboratories. A well plate typically has 6, 12, 24, 48, 96, 384 or 1536 cavities arranged in a 2:3 rectangular matrix, but other configurations are available. Many well plates conform to the SLAS (Society for Laboratory Automation and Screening) standard which defines the well plate footprint as measuring 127.76 mm×85.48 mm (the height of a well plate conforming to the SLAS standard may vary). Each well of a well plate typically holds somewhere between tens of nanoliters to several milliliters of fluid. Cavities can be either circular or square.

The cavities of a well plate are closed at the bottom and open at the top, unlike pipette tips which have openings at both the top and bottom. Because the cavities of a well plate only have openings at the top, the devices and methods for washing pipette tips (such as the devices and methods disclosed in the above-referenced co-owned patents) cannot be used to wash well plates.

BRIEF SUMMARY OF THE DISCLOSURE

One embodiment of the invention comprises a device for cleaning one or more items, each item to be cleaned defining a plurality of cavities. The device comprises an enclosure defining a wash chamber, a rotor positioned within the wash chamber and selectively rotatable about an axle, a motor for selectively rotating the axle and thereby selectively rotating the rotor, a dispenser, and a drain. The rotor comprises a plurality of holders spaced about the axle, each holder adapted to selectively receive and hold a respective item to be cleaned such that the cavities of each item to be cleaned are facing away from the axle. The rotor is selectively rotatable into and stoppable at each of a plurality of different orientations, the number of different orientations being equal to or greater than the number of holders such that each of the plurality of holders is in a respective different position when the rotor is in each of the plurality of different orientations. The dispenser comprises at least one liquid input and at least one liquid output. The dispenser is positioned such that the at least one liquid output is adapted to operably direct cleaning fluid to contact a different one of the items to be cleaned to clean material out of the cavities when the rotor is in a respective different orientation and the plurality of items to be cleaned are held by their respective holder. The drain is for draining the cleaning fluid out of the chamber. The rotor is selectively rotatable at a predefined rotational speed for a predefined amount of time, such that the rotation of the rotor is adapted to expel the cleaning fluid operably directed by the dispenser from the cavities of each item to be cleaned.

The dispenser may comprise a manifold dispenser comprising at least one liquid input and a plurality of liquid outputs. A number of liquid outputs of the manifold dispenser may be equal to a number of cavities of each item to be cleaned such that each one of the fluid outputs operably directs fluid at a corresponding one of the cavities. The manifold dispenser may be capable of being raised and lowered vertically relative to the rotor. The manifold dispenser may be capable of being raised to a position in which the manifold dispenser does not obstruct the selective rotation of the rotor. The manifold dispenser may be capable of being lowered to a position in which the manifold dispenser is positioned a predefined distance apart from the item to be cleaned at which the manifold dispenser is to operably direct the cleaning fluid.

The chamber may be at least partially fillable with cleaning fluid to create a reservoir of cleaning fluid such that each item to be cleaned is fully submerged in cleaning fluid at least once during each complete rotation of the rotor. The rotor may be selectively rotatable back-and-forth such that the rotor is adapted to move a fully submerged item to be cleaned back-and-forth within or repeatedly in-and-out of the reservoir of cleaning fluid. The device may further comprise one or more transducers capable of outputting sound in an ultrasonic range into the wash chamber and into the reservoir of cleaning fluid.

The device may further comprise one or more ultraviolet (UV) lights positioned to emit UV light into the wash chamber and at one or more items to be cleaned.

The one or more items to be cleaned may comprise one or more pieces of laboratory equipment. The one or more pieces of laboratory equipment may comprise one or more well plates.

Alternative embodiments of the invention may comprise a method of for cleaning one or more items, each item to be cleaned defining a plurality of cavities. The method comprises providing a cleaning device as described herein, receiving each item to be cleaned in sequence by a respective holder when the rotor is in a respective orientation, rotating, in between the receiving of each item to be cleaned, the rotor to a subsequent orientation in which a respective holder is open, spraying cleaning fluid at each item to be cleaned in sequence, rotating the rotor in between spraying each piece to move each successive item to be cleaned into position to be cleaned, until all items to be cleaned have been sprayed with cleaning fluid, and rotating the rotor at the predefined rotational speed for the predefined amount of time to expel cleaning fluid from the cavities of each item to be cleaned.

The method may further comprise, prior to rotating the rotor, raising the manifold dispenser to a position in which the manifold dispenser does not obstruct the rotation of the rotor. The method may further comprise, prior to spraying each item to be cleaned, lowering the manifold dispenser to a position in which the manifold dispenser is positioned a predefined distance apart from the item to be cleaned that is to be sprayed.

The method may further comprise at least partially filling the wash chamber with cleaning fluid to create a reservoir of cleaning fluid such that each item to be cleaned is fully submerged in cleaning fluid at least once during each complete rotation of the rotor. The method may further comprise rotating the rotor back-and-forth such that a fully submerged item to be cleaned is moved back-and-forth within or repeatedly in-and-out of the reservoir of cleaning fluid.

The method may further comprise outputting, via one or more transducers, sound in an ultrasonic range into the wash chamber and into the reservoir of cleaning fluid.

The method may further comprise emitting, via one or more ultraviolet (UV) lights, UV light into the wash chamber and at one or more items to be cleaned.

Alternative embodiments of the invention may comprise a device for cleaning one or more items, each item to be cleaned defining a plurality of cavities. The device comprises an enclosure defining a wash chamber, a plurality of cleaning operation mechanisms positioned spaced about the axle within the wash chamber, a rotor positioned within the wash chamber and selectively rotatable about an axle, and a motor for selectively rotating the axle and thereby selectively rotating the rotor. Each of the plurality of cleaning operation mechanisms are adapted to perform a cleaning operation upon an adjacent one of the items to be cleaned. The rotor comprises two or more holders spaced about the axle. Each holder is adapted to selectively receive and hold a respective item to be cleaned such that the cavities of each item are facing away from the axle. The rotor is selectively rotatable into and stoppable at a number of different orientations equal to the number of different cleaning operation mechanisms such that each of the holders and any item to be cleaned held thereby is in a position to be acted upon by the respective cleaning operation mechanism at that orientation. At least one of the plurality of cleaning operation mechanisms comprises a cleaning fluid dispenser. The dispenser comprises at least one liquid input and at least one liquid output. The dispenser is positioned such that the at least one liquid output is adapted to operably direct cleaning fluid to contact a different one of the items to be cleaned to clean material out of the cavities when the rotor is in each of the different orientations. The rotor is selectively rotatable at a predefined rotational speed for a predefined amount of time, such that the rotation of the rotor is adapted to expel cleaning fluid from the cavities of each item to be cleaned that has cleaning fluid in any of its cavities.

The rotor may be selectively rotatable to two or more successive different orientations such that an item to be cleaned that is held by one of the holders can undergo a sequence of cleaning operations by different ones of the plurality of cleaning operation mechanisms.

At each of the different orientations, an item to be cleaned that is held by one of the holders may undergo a cleaning operation by one of the plurality of cleaning operation mechanisms while a different item to be cleaned that is held by a different one of the holders can undergo a different cleaning operation by a different one of the plurality of cleaning operation mechanisms.

The device may further comprise a drain for draining the cleaning fluid out of the chamber.

The axle may comprise a horizontal axle.

The dispenser may comprise a manifold dispenser comprising at least one liquid input and a plurality of liquid outputs. A number of liquid outputs of the manifold dispenser may be equal to a number of cavities of each item to be cleaned such that each one of the fluid outputs operably directs fluid at a corresponding one of the cavities. The manifold dispenser may be capable of being raised and lowered vertically relative to the rotor. The manifold dispenser may be capable of being raised to a position in which the manifold dispenser does not obstruct the selective rotation of the rotor. The manifold dispenser may be capable of being lowered to a position in which the manifold dispenser is positioned a predefined distance apart from the item to be cleaned at which the manifold dispenser is to operably direct the cleaning fluid.

The chamber may be at least partially fillable with cleaning fluid to create a reservoir of cleaning fluid such that each item to be cleaned is fully submerged in cleaning fluid at least once during each complete rotation of the rotor. At least one of the plurality of cleaning operation mechanisms may comprise the reservoir of cleaning fluid.

The rotor may be selectively rotatable back-and-forth such that the rotor is adapted to move a fully submerged item to be cleaned back-and-forth within or repeatedly in-and-out of the reservoir of cleaning fluid. The device may further comprise one or more transducers capable of outputting sound in an ultrasonic range into the wash chamber and into the reservoir of cleaning fluid.

The device may further comprise one or more ultraviolet (UV) lights positioned to emit UV light into the wash chamber and at one or more items to be cleaned. At least one of the plurality of cleaning operation mechanisms may comprise the one or more UV lights.

The one or more items to be cleaned may comprise one or more pieces of laboratory equipment. The one or more pieces of laboratory equipment may comprise one or more well plates.

BRIEF DESCRIPTION OF THE SEVERAL VIEWS OF THE DRAWING(S)

The foregoing summary, as well as the following detailed description of the disclosure, will be better understood when read in conjunction with the appended drawings. For the purpose of illustrating the disclosure, there are shown in the drawings embodiments which are presently preferred. It should be understood, however, that the disclosure is not limited to the precise arrangements and instrumentalities shown. In the drawings.

DETAILED DESCRIPTION

Figure 1:
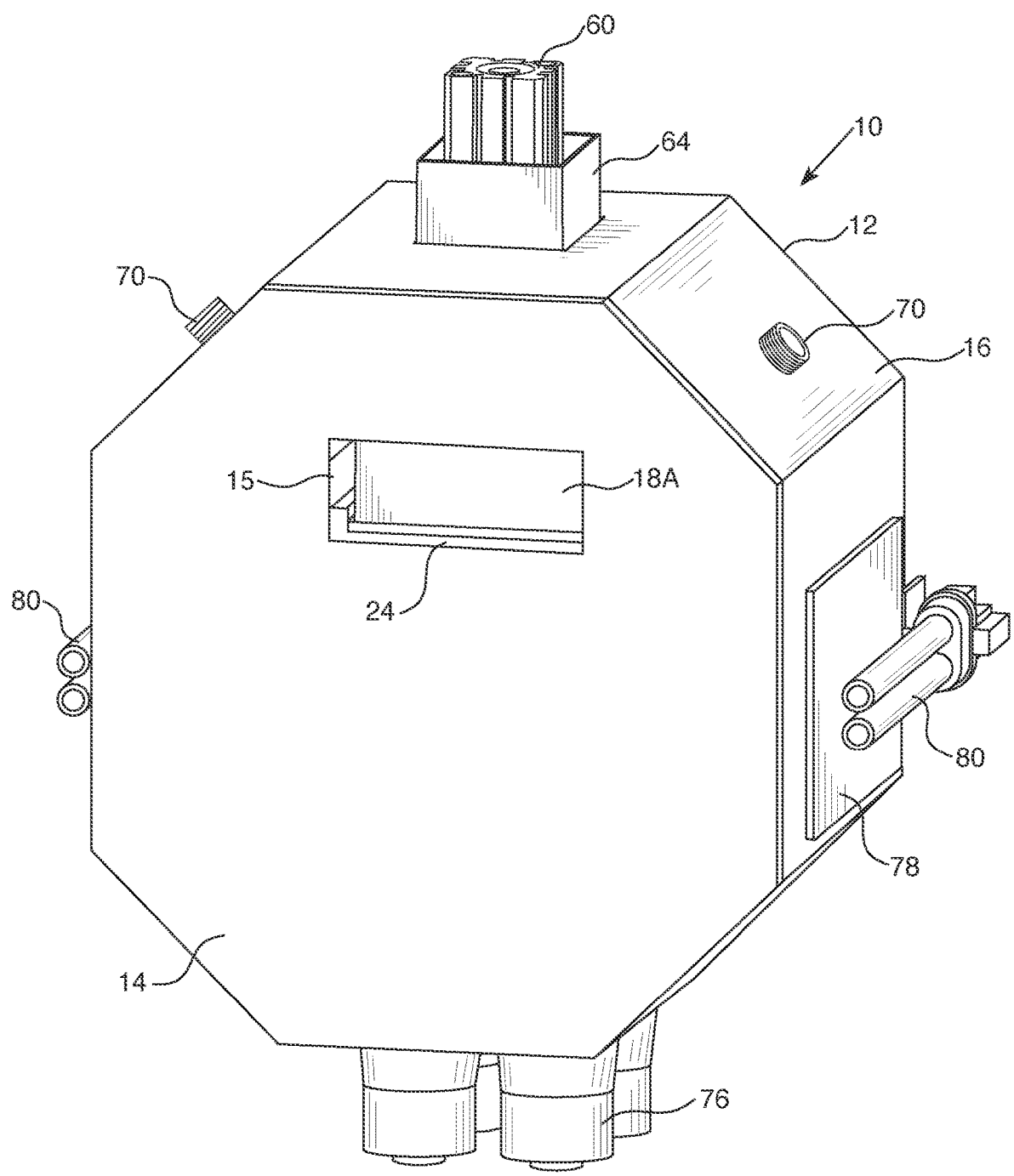
FIG. 1 illustrates a front perspective view of a well plate washing device, in accordance with embodiments of the invention.

Embodiments of the invention comprise devices and methods for washing, drying, and/or sanitizing laboratory consumables, particularly laboratory consumables having one or more cavities with open top ends and closed bottom ends, including but not limited to well plates, microtiter plates, deep well plates, PCR plates, and reagent troughs and reservoirs, so that the laboratory consumables may be reused for additional experiments/reactions. Embodiments of the invention will typically remove any chemical reagents and biomolecules used in the plate cavities during an experiment, remove any environmental contaminants, and sanitize the plate.

For simplicity, embodiments of the invention are described herein in relation to washing laboratory consumables, mainly well plates and the like. However, devices and methods of embodiments of the invention could be used to wash labware that is not consumable, such as some reagent basins and laboratory glassware. Further, devices and methods of embodiments of the invention could be used to wash items that are not necessarily used in laboratories. The device and method described herein could be extended to other fields and uses in the future, including but not limited to, janitorial equipment, hospital equipment, kitchenware, food processing equipment, farming equipment, car parts, textiles, or any other commercial or personal objects that need to be cleaned and/or sanitized.

Embodiments of the invention use a fluid manifold to spray cleaning solution into the open top end of each cavity of a well plate, and then spin the device around a central axis such that centrifugal force causes some or all of any fluid remaining in the cavities to be ejected. Embodiments of the invention may also fully submerge a well plate in water or a cleaning solution (either of which are referred to generically herein as "cleaning fluid") as part of the cleaning process. Embodiments of the invention may use a spray nozzle or other mechanism, instead of the manifold described in this disclosure, to provide a jet of pressurized fluid or otherwise transport fluid to contact or interact with the object being cleaned.

An exemplary well plate washing device 10 of embodiments of the invention is illustrated in FIGS. 1-11. The well plate washing device 10 comprises an outer housing 12 defining a wash chamber 13. The outer housing 12 comprises a side wall 16 having eight generally planar panels arranged in an octagonal cylinder configuration, a rear wall 17, and a front panel 14. The housing 12 may be constructed of any suitable material, typically any chemically-resistant material such as plastic or stainless steel. The rear wall 17 may be affixed to the side wall 16 in any suitable manner (e.g., welding) so as to prevent fluid leakage from any seams. The wash compartment rear wall and sides may be detachable from each other in any suitable manner, including using fasteners or latches to mount them together in conjunction with a seal or gasket. The front panel 14 is typically selectively removably affixed to the side wall 16 to provide access to the internal components and the wash chamber 13 as needed (e.g., for maintenance). A gasket (not illustrated) or the like may be used between the front panel 14 and the side wall 16 to prevent fluid leakage. The front panel 14 may be secured to the side wall 16 using any suitable mechanism or method. While the sidewall is illustrated having an octagonal configuration, any other suitable configuration (e.g., round cylinder) may be used.

An opening 15 is defined in the front panel 14 for loading and unloading well plates 18A, 18B into and out of the wash chamber 13. A door or other suitable covering (not illustrated) may be used to selectively provide access to the wash chamber 13 for loading and unloading and to close off the opening 15 during a wash cycle to prevent any fluid from exiting through the opening 15. The well plates may be manually loaded and unloaded through the opening 15. Alternatively, any suitable automated loading/unloading mechanism (not illustrated) may be used to load and unload well plates through the opening 15 into the wash chamber 13. Such a loading/unloading mechanism may interface with a more extensive material handling system capable of transporting well plates to and from the device 10.

Embodiments of the invention include a mechanism for receiving one or more well plates, holding the well plates in position while water or a cleaning solution is sprayed into the cavities, and rotating the well plates about an axis to remove fluid from the cavities. The rotational axis depicted in this exemplar is horizontal, but other embodiment of the device may use a vertical, diagonal, or other axis of rotation. This mechanism is almost entirely contained within the housing 12. As such, all of the components of this mechanism should be resistant to whatever fluids are used in the cleaning process. A selectively rotatable horizontal axle or shaft 22 is supported at one or more locations (e.g., the front panel 14 and the rear wall 17) via bearing 28 (the front bearing is not illustrated). A vibration-damping coupling 30 connects the axle 22 to a motor 32. The coupling 30 is vibration-damping to minimize or prevent undesirable vibration during rotor rotation. This may allow the device to conduct a wash process in the event of uneven loading of well plates (e.g., when one or three plates are loaded). Any suitable motor may be used. In one embodiment of the invention, the motor 32 comprises a DC stepper motor. The shaft 22 may be keyed as illustrated to facilitate securing the rotor (described below) to the shaft. Other methods of securing the rotor to the shaft may be used in alternate embodiments of the device. The motor 32 can spin the well plates at a high rpm (revolutions per minute), rotate the well plates to specific angular positions, or do movement patterns for "rotary agitation."

The shaft 22 protrudes through a center hole in a rotor 20. The rotor 20 may be cross or X-shaped, as illustrated, with four equal length arms positioned substantially at right angles to each other. In other embodiments of the device, "arms" may refer to other support structures, not necessarily in a cross shape. The number of arms of the rotor correlates to the number of well plates that can be washed at one time by the device; greater or fewer than four arms may be used. The rotor 20 is preferably weighted to dampen vibration, and as such is typically constructed of any suitable material with proper chemical resistances (e.g., plastic or stainless steel). A spacer (not illustrated) may be placed between the shaft 22 and the rotor 20 to provide a friction fit to help retain the rotor 20 on the shaft 22. One or more set screws or the like (not illustrated) may also be used to secure the rotor 20 to the shaft 22.

Figure 2:
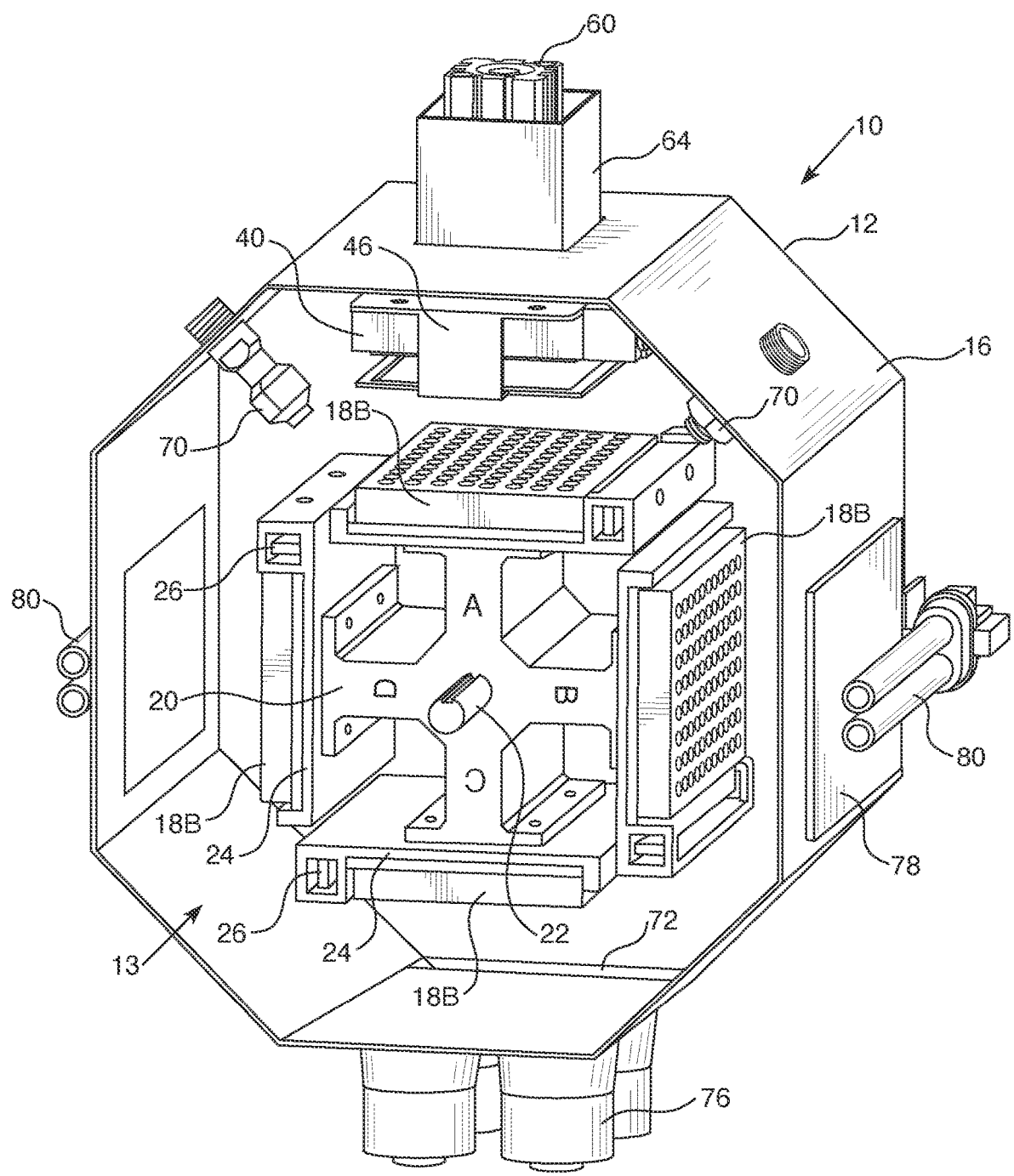
FIGS. 2-5 illustrate front perspective views of the well plate washing device of FIG. 1, with the front cover removed.

A plate holder 24 is affixed at the distal or outer end of each arm of the rotor 20, using any suitable mechanism for affixation. This plate holder may also be constructed as a part of the rotor. In the illustrated embodiment there are four plate holders 24, such that the device 10 can receive, hold, and wash up to four well plates at one time. Other embodiments of the device may be able to wash greater or fewer than four objects at once, but generally greater than one object in most efficient usage. For illustrative purposes, the arms of the rotor 20 are labeled with letters A-D to indicate the four different well plate positions. During the process of adding or removing well plates from the device and during the process of washing the well plates, the rotor 20 is typically rotated to four different angular positions. In each of these four angular positions, two of the opposing arms of the rotor 20 are aligned substantially vertically and the other two opposing arms are aligned substantially horizontally. That is, in each of these four angular positions, one well plate (A in FIG. 2) is in the top or 12 o'clock position, one well plate (B in FIG. 2) is in the right or 3 o'clock position, one well plate (C in FIG. 2) is in the bottom or 6 o'clock position, and one well plate (D in FIG. 2) is in the left or 9 o'clock position. In FIG. 2, the plate holder on the arm labeled A is in the top position, the plate holder on the arm labeled B is in the right position, the plate holder on the arm labeled C is in the bottom position, and the plate holder on the arm labeled D is in the left position, Each plate holder 24 holds a single well plate during the wash cycle. In the illustrated embodiment, each plate holder 24 comprises a planar base and raised side and rear walls. The front edge of the plate holder 24 is not raised to enable a well plate to be slid horizontally into the plate holder 24 through the opening 15. Any suitable mechanism may be used to hold the well plate onto the plate holder 24. In the illustrated embodiment, a gripper bar 26 forms one raised side wall of the plate holder 24. One or more springs or the like (not illustrated) bias the gripper bar 26 toward the well plate to apply a restraining force, thereby sandwiching the well plate between the gripper bar 26 and the opposing raised side wall of the plate holder 24. Other embodiments of the device may use different mechanisms that apply forces to hold the objects in position on the rotor during rotation.

In the illustrated embodiment, the plate holders 24 are configured to receive well plates having a predetermined footprint (i.e., length and width), typically based on the ANSI/SLAS microplate standard (formerly called the SBS standard), but having a variety of different heights. Two different height well plates are illustrated in the figures—a "tall" well plate 18A and a "short" well plate 18B. Other embodiments of the device may allow for objects with different shapes, dimensions, and geometries to be held in position on the rotor. This may be accomplished through the use of specifically designed holders for specific objects, adapters, or other modular holding mechanisms.

The front panel opening 15 aligns with the top well plate position, such that a well plate is loaded into or removed from the plate holder 24 in the top position. After a well plate is loaded into the plate holder 24 in the top position (manually or by an automated material handling mechanism), the motor 32 activates and rotates the rotor 20 90° such that an adjacent plate holder 24 is now in the top position. (The rotor may be rotated clockwise or counterclockwise. The rotation of the rotor will be described herein only as clockwise for simplicity.) The amount of rotation of the rotor may be controlled by counting the steps of the stepper motor and/or by using one or more sensors to verify the position of the rotor. After the rotor 20 is rotated 90°, another well plate may be loaded into the plate holder 24 that is now in the top position. This may be repeated two more times until a well plate has been loaded into all four plate holders 24. Other embodiments of the device may load objects in locations or orientations other than the top position. A wash cycle (described below) may then be run to clean and disinfect the well plates. The cleaned well plates may then be removed from the device 10 in a similar fashion, that is, one at a time from the top position. Embodiments of the invention may enable the device to operate without all of the plate holders 24 loaded. If only two well plates are to be loaded, the rotor 20 may be rotated 180° to ensure that the well plates are loaded onto opposing (rather than adjacent) plate holders 24 for balancing purposes.

One or more sensors 96 may be used to detect the presence of a well plate in a plate holder. Any suitable number, position, and/or type of sensors may be used (including but not limited to optical, ultrasonic, infrared, mechanical, and/or magnetic sensors). A single sensor may be used, for example, adjacent the top position to detect that a well plate has been loaded prior to rotating the rotor 20 or adjacent the right side position (position B in FIG. 2) to detect the well plate after rotating the rotor 20. Alternatively, there may be a sensor at each of the four well plate positions (i.e., top, right, bottom, left).

The well plate in the top position may be sprayed with a fluid (e.g., cleaning solution, rinsing agent, etc.) by a fluid manifold 40. The fluid manifold 40 is positioned above the well plate that is in the top position and sprays fluid downward onto the top of that well plate. The well plates are positioned on the plate holders 24 such that the top openings of the cavities face outward (away from the center axis). In this regard, the top openings of the cavities of the well plate in the top position face toward the fluid manifold 40, thereby enabling the fluid sprayed from the fluid manifold 40 to enter the cavities of that well plate. The fluid manifold 40 has a generally rectangular prism shape, with a fluid input 42 on the top surface (the location of the fluid input may vary) and a plurality of fluid outputs 44 arranged in a matrix on the bottom surface. One or more pumps 98 may be used to pump the fluid to the fluid manifold 40 from a reservoir (not illustrated) via a hose (not illustrated). The pump 98 may be used to drive the pressurized fluid wash. Alternatively, pump 98 may be used to prime the lines (fill the tubes leading to manifold port 42 with fluid), and then compressed air may be used to provide a greater pressure fluid movement, as described below. A plurality of channels (not illustrated) defined within the fluid manifold 40 direct the fluid from the fluid input 42 to each of the fluid outputs 44. The fluid then sprays downward from the fluid outputs 44 toward the well plate in the top position. It is desirable that the fluid exit the fluid manifold 40 at a sufficient pressure to enter the cavities of the well plate with sufficient force to dislodge any materials within the cavities. The amount of fluid pressure needed may vary. A pressure regulator (not illustrated) may be used to set the wash pressure to different values as needed. The pump pressure (or air pressure of the fluid that is driven by air, as described below), as well as narrowing of the channels between the fluid input 42 and the fluid outputs 44 of the fluid manifold 40, provide the desired fluid output pressure.

In the illustrated embodiment, the fluid manifold 40 has 96 fluid outputs 44 arranged in an 8×12 matrix to correspond to the cavity arrangement of a conventional 96 cavity well plate. Different fluid manifolds with different numbers and arrangements of fluid outputs may be alternatively used to correspond to well plates having different numbers and arrangements of cavities. Such different fluid manifolds may be readily interchangeable within the device. Further alternatively, fluid manifolds having wider angle spray nozzles may be used such that there need not be a one-to-one correspondence between fluid outputs of the fluid manifold and well plate cavities. Other embodiments of the invention may use a spray nozzle or other dispensing mechanism, instead of the manifold described in this disclosure, to provide a jet of pressurized fluid or otherwise transport fluid to contact or interact with the object(s) being cleaned.

It may be desirable to spray air into the cavities of the well plate. Some of the above-referenced co-owned patents describe alternating spraying fluid and spraying air from the fluid outputs of the fluid manifold, and the mechanisms/ methods described therein may be used in embodiments of the present invention. Similarly, pump 98 may be used to prime the lines (fill the tubes leading to manifold port 42 with fluid), and then compressed air may be used to provide a greater pressure fluid movement. The well plate washing device of embodiments of the invention may use the same or a similar method to spray air through the fluid manifold 40, using a pump 98 or otherwise pressurized air, to help clean the cavities and/or remove cleaning fluid from the cavities. The pressurized air flow may be generated from an appropriate source, such as a blower, fan, pump, vacuum, or air compressor. The device may alternate the spraying of the cleaning fluid and air or may spray air after spraying the cleaning fluid to help remove the cleaning fluid before the plates are rotated.

Figure 10A:
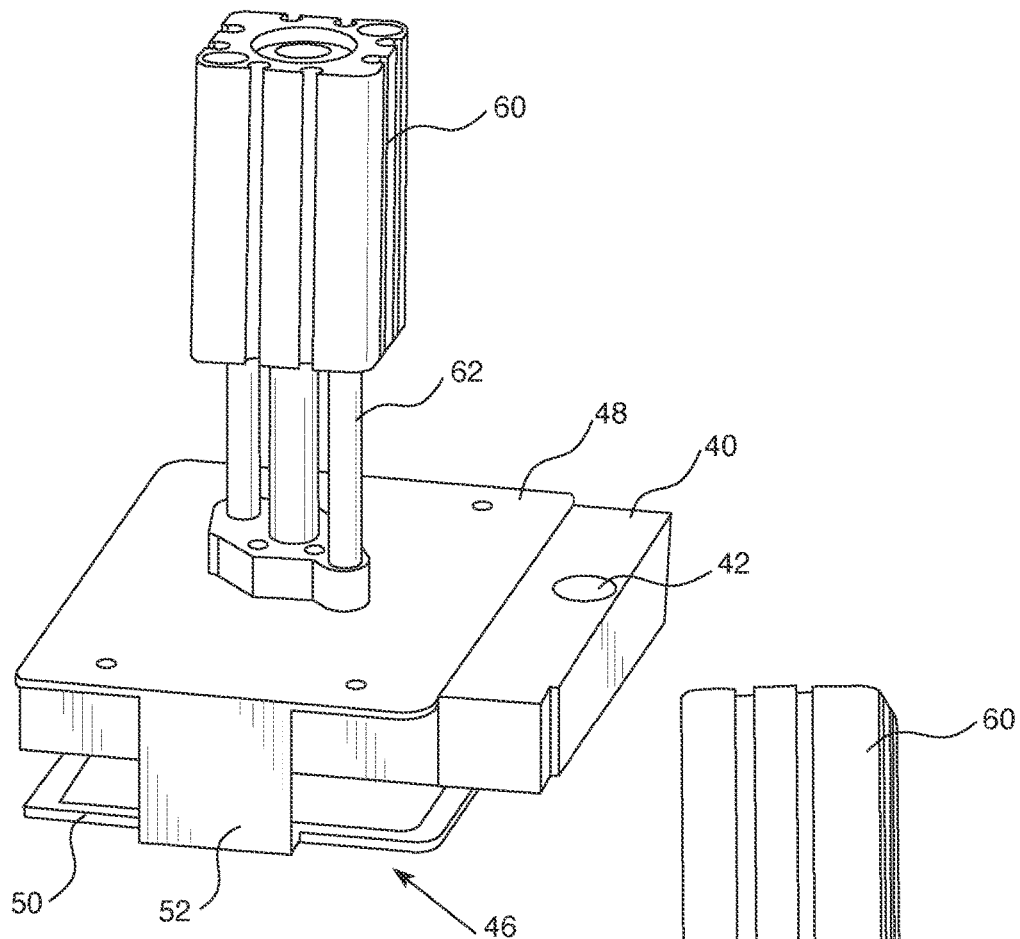
FIGS. 10A and 10B illustrate, respectively, top and bottom perspective views of the mechanism for raising and lowering the fluid manifold of the well plate washing device of FIG. 1, removed from the device for visibility.
Figure 10B:
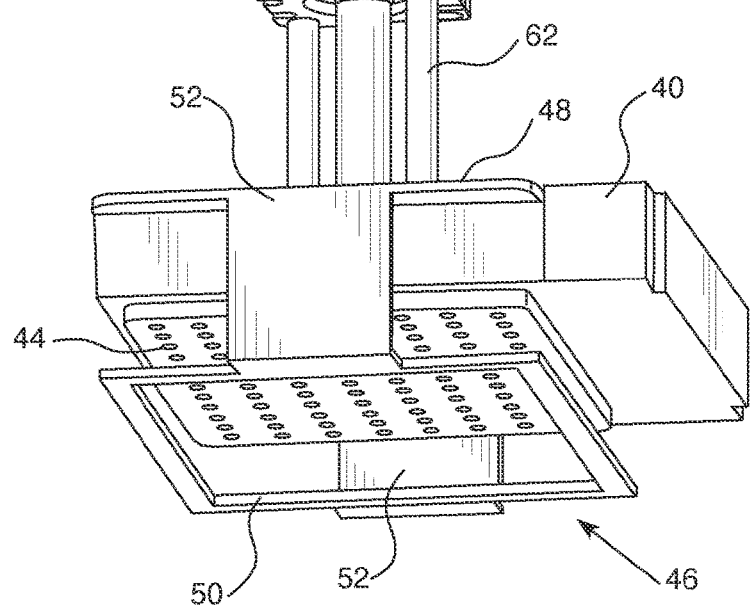

Because the cavities of well plates are only open on the top end, the cleaning fluid must both enter and exit the cavities through the open top end. Because of this, the fluid manifold cannot seal against the top of the well plate as there would be no way for the fluid to escape. In this particular embodiment of the device, to maintain the necessary spacing between the fluid manifold and the well plate, a spacer 46 is used. As best seen in FIGS. 10A and 10B, the spacer 46 comprises a top plate 48 to which the manifold is affixed, a bottom frame 50, and an arm 52 therebetween. As seen in the figures, the bottom frame 50 comprises an open rectangle that is sized and shaped to contact the outer edge of the top surface of the well plate to maintain the desired spacing while not obstructing the fluid flow from the fluid manifold 40 to the well plate. The spacer 46 of the illustrated embodiment maintains a 12 mm spacing between the bottom surface of the fluid manifold 40 in the top surface of the well plate, but any suitable spacing may be used. Any other suitable method to create the proper spacing may also be used.

The fluid manifold 40 is selectively movable up and down relative to the well plate in the top position. In the up position, the fluid manifold 40 is out of the path of the well plates, plate holders 24, and rotor 20 as the rotor 20 rotates. When the rotor 20 stops rotating, the fluid manifold 40 may be lowered into position to spray fluid at the well plate in the top position. Any suitable mechanism may be used to selectively raise and lower the fluid manifold 40. In the illustrated embodiment, the fluid manifold 40 is affixed (via the spacer 46) to a linear actuator 60 with selectively extendable and retractable arms 62. The linear actuator 60 extends the arms 62 to lower the fluid manifold 40 and retracts the arms 62 to raise the fluid manifold 40. Because well plates of different heights may be washed in the device 10, the stroke length of the linear actuator 60 must be sufficient to be able to lower the fluid manifold 40 to a low enough position to reach the top surface of the shortest well plates that may be washed in the device 10. In a preferred embodiment of the invention, a simple pneumatic linear actuator is used in which the arms 62 extend until the spacer 46 contacts the top surface of the well plate. When the spacer 46 contacts the top surface of the well plate, the linear actuator 60 will continue to try to extend the arms 62 and in this regard will maintain sufficient pressure to hold the fluid manifold 40 in position, despite the fluid spray applying an opposing force. It is desirable that the linear actuator provide enough force to maintain the position of the fluid manifold but not excessive force that might damage the well plate, the plate holder 24, the rotor 20, or any other components of the device 10. Because this mechanism automatically adjusts to any height well plate, it is possible to wash well plates having different heights in the same wash cycle. In alternative embodiments of the invention, a multi-position pressure-sensitive linear actuator may be used to raise and lower the fluid manifold to a plurality of different positions depending on the height of the well plate, however such an embodiment is significantly more complex. Any suitable sensor (such as a Hall effect sensor) or other mechanism may be used to verify that the fluid manifold 40 is raised to its fully retracted position such that the rotor 20 can safely rotate.

Figure 3:
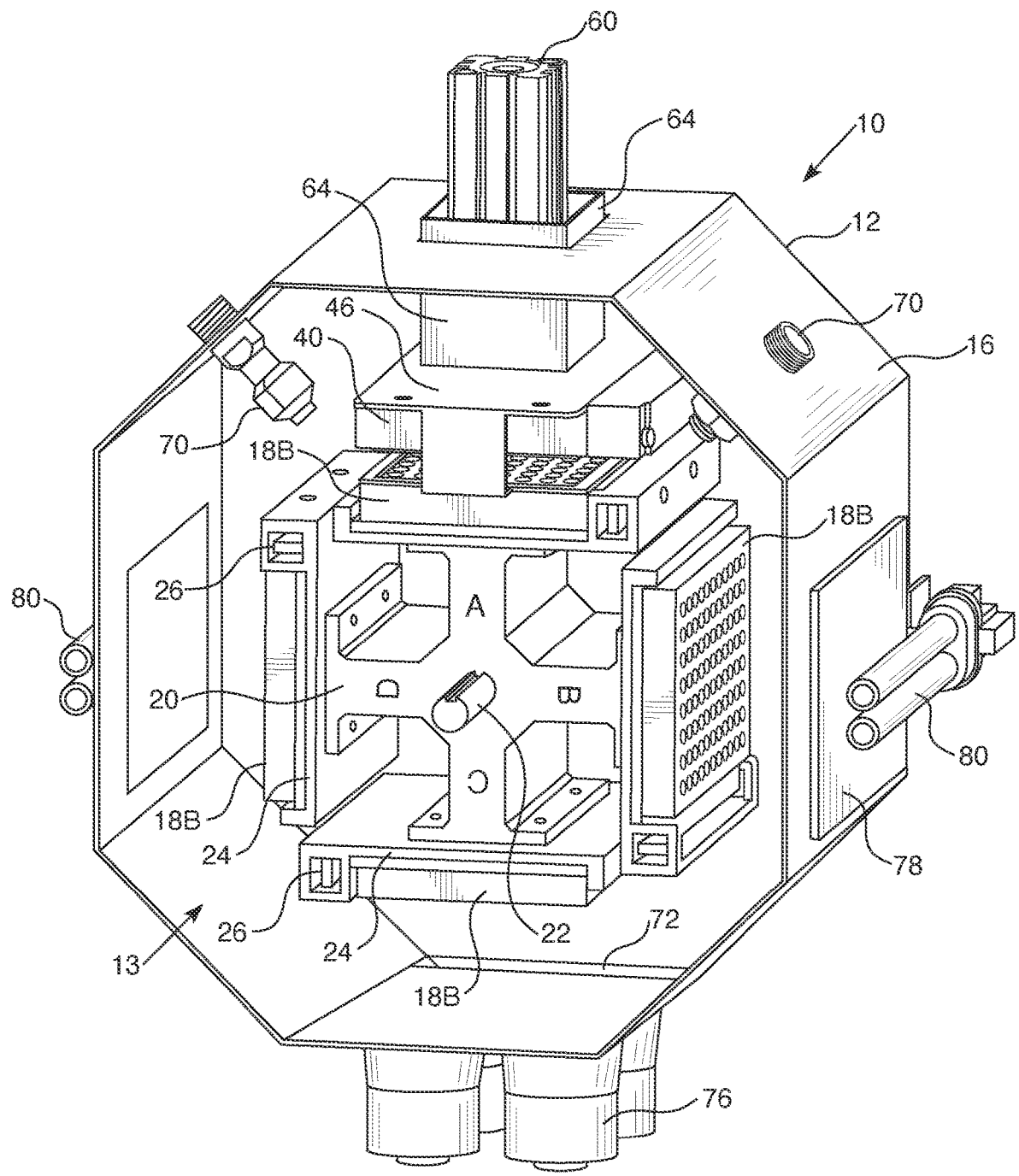
Figure 4:
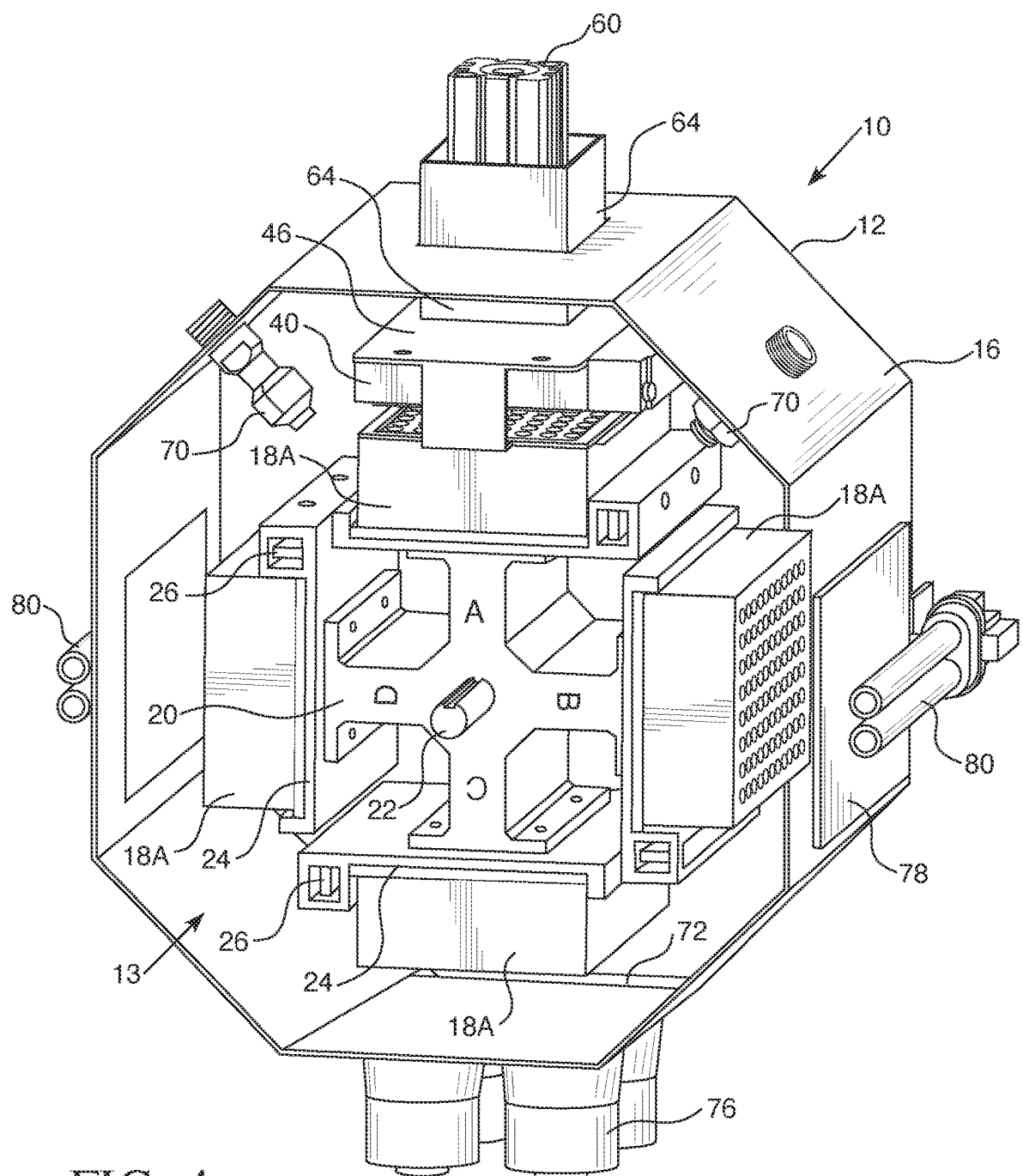
Figure 5:
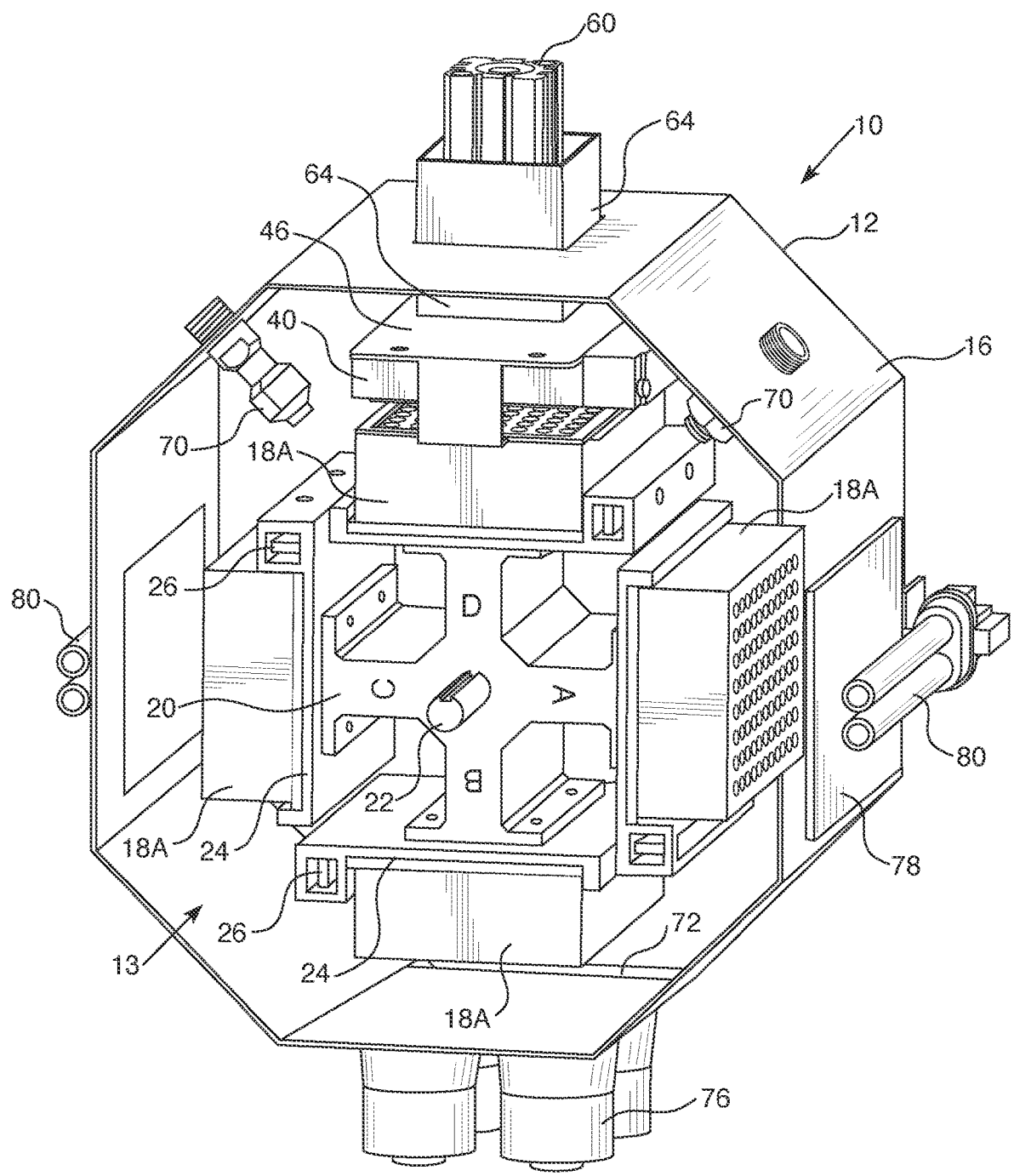
Figure 6:
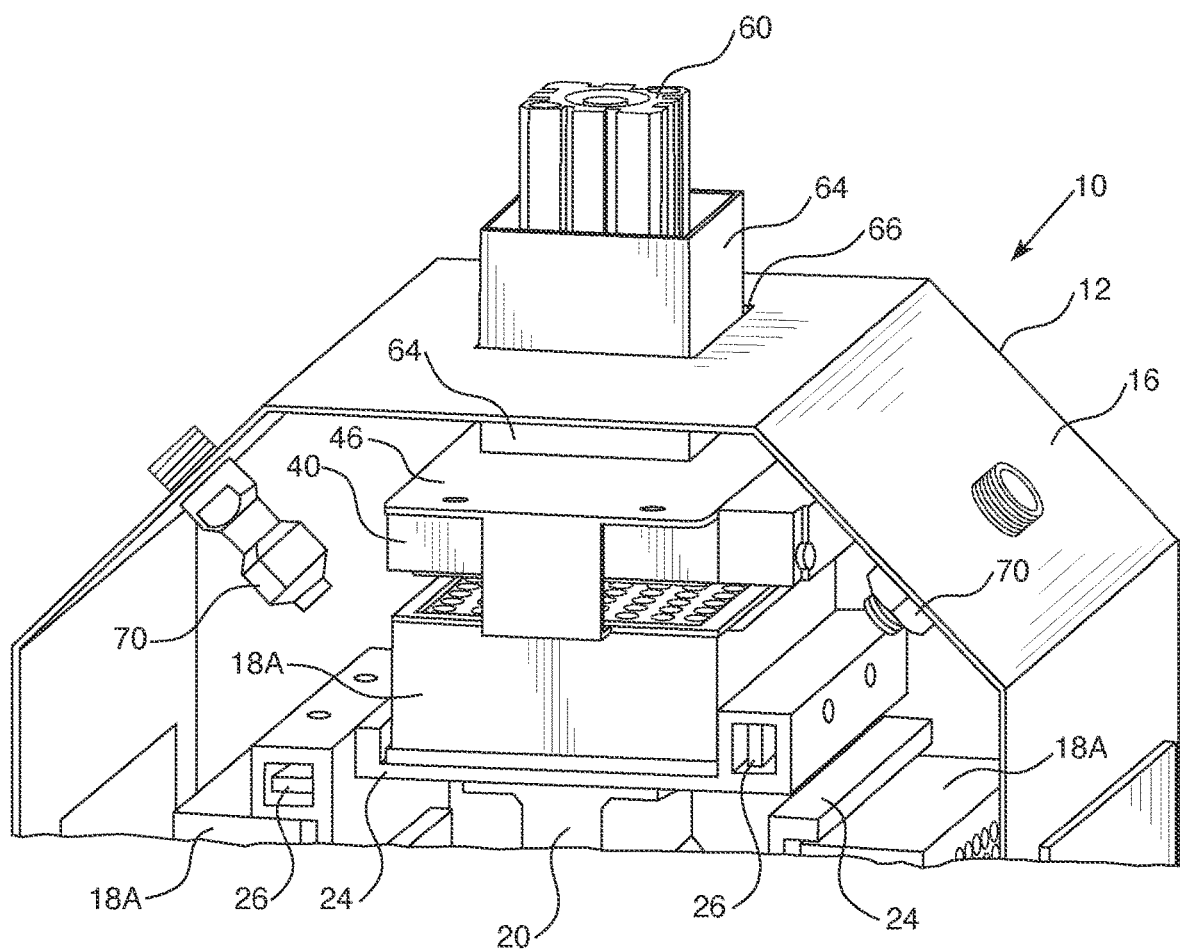
FIG. 6 illustrates a close-up front perspective view of a portion of the well plate washing device of FIG. 1.
Figure 7:
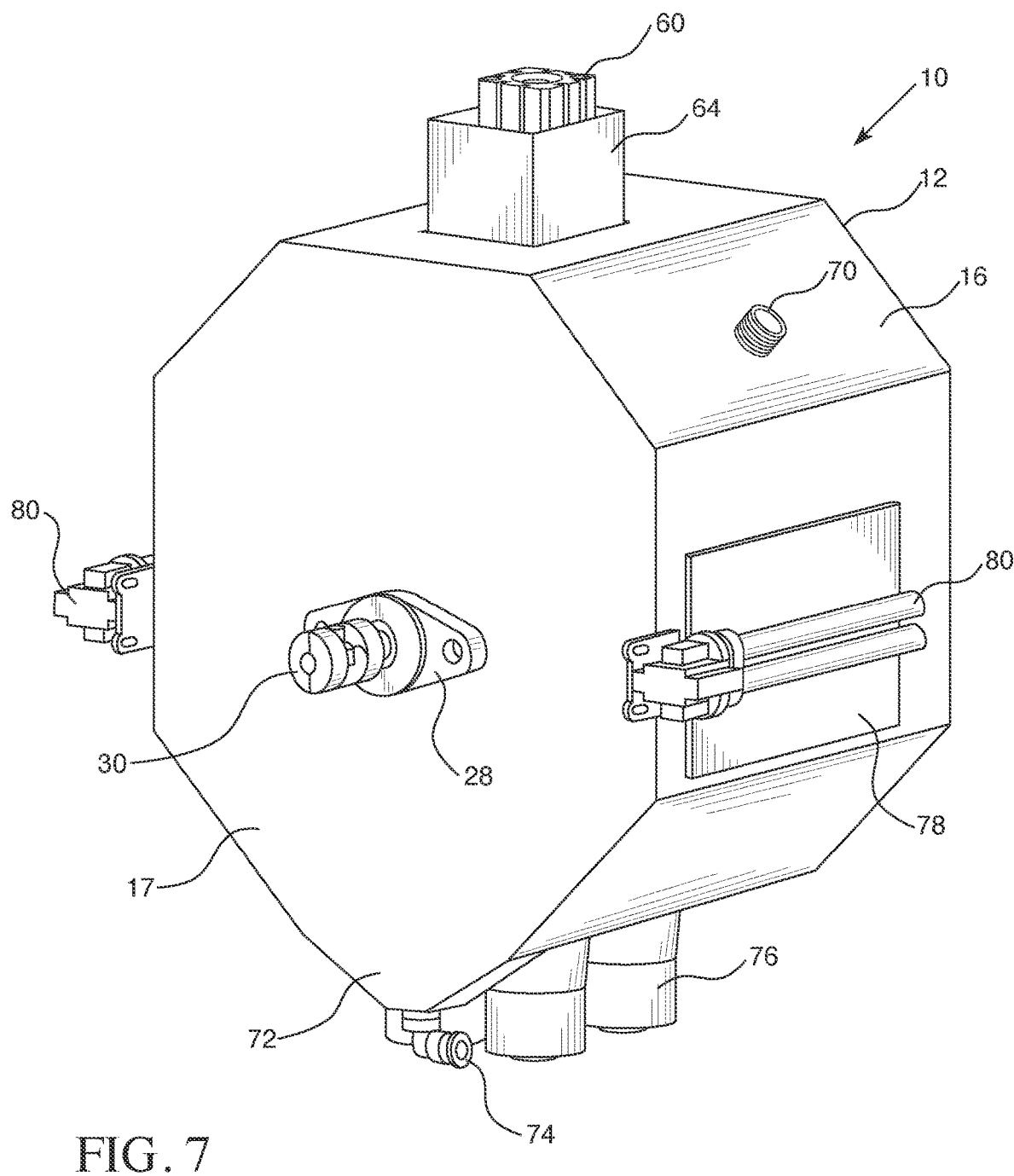
FIG. 7 illustrates a rear perspective view of the well plate washing device of FIG. 1.
Figure 8:
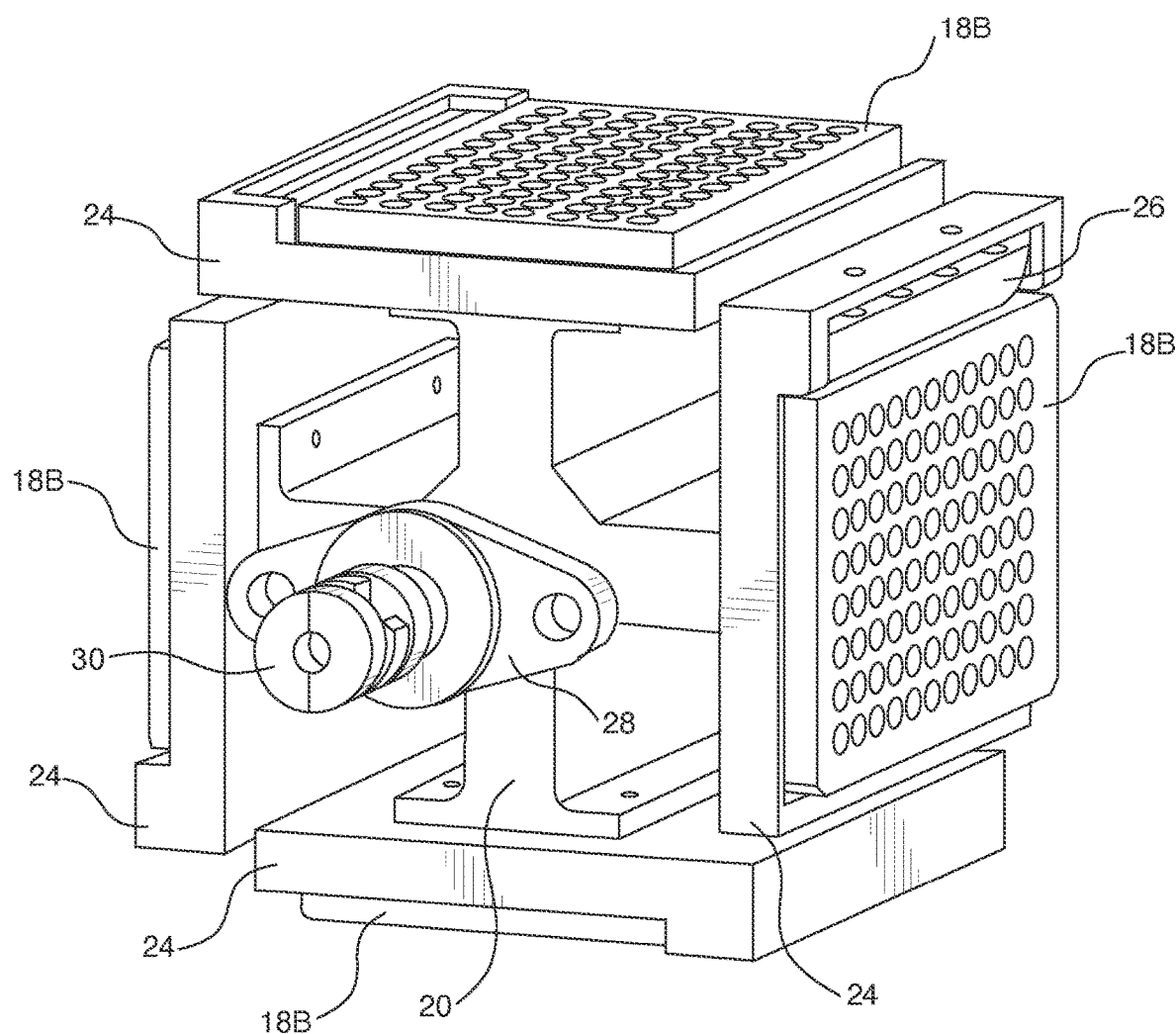
FIGS. 8 and 9 illustrate, respectively, rear and front perspective views of the rotating portion of the well plate washing device of FIG. 1, removed from the device for visibility.
Figure 9:
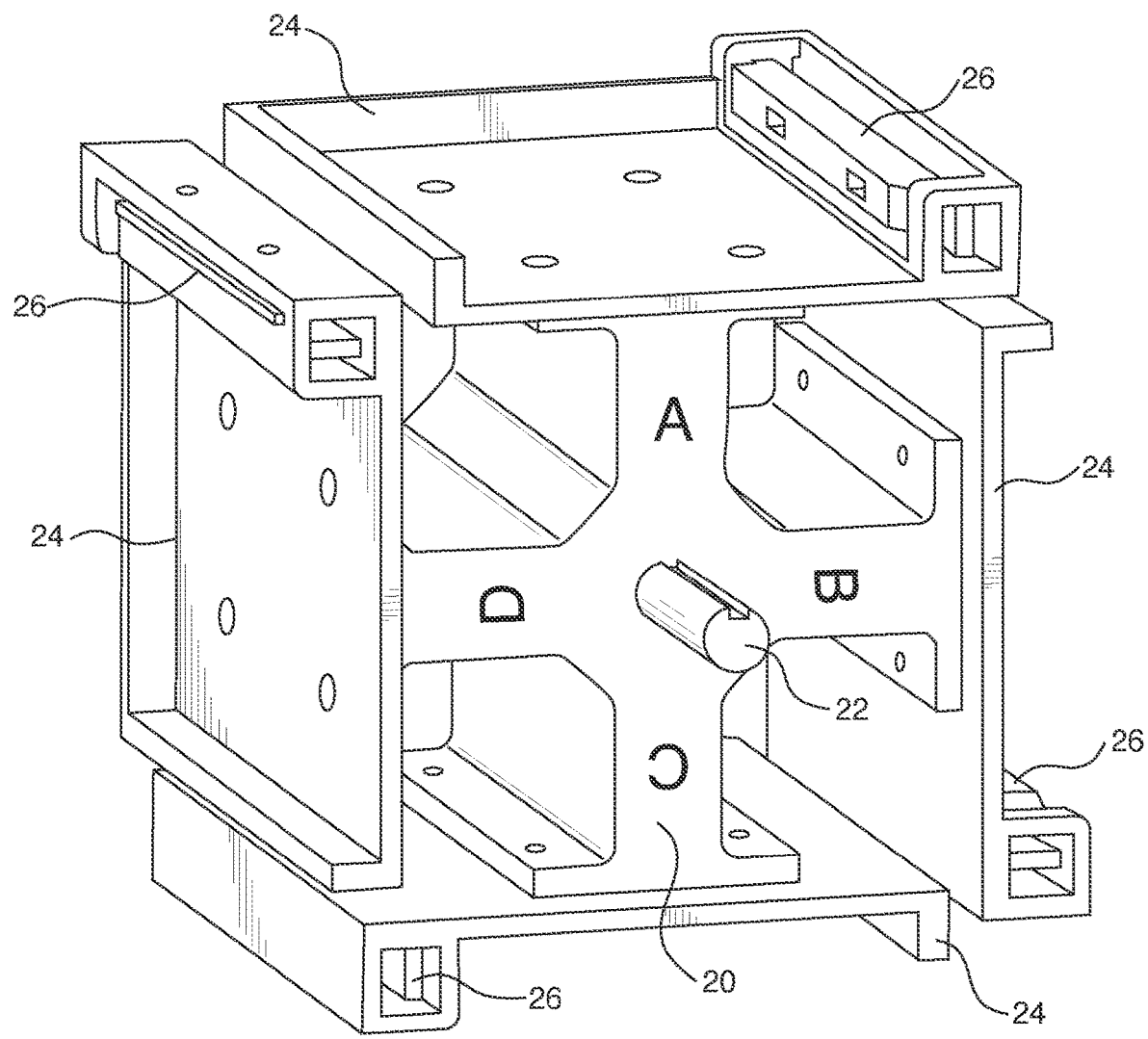

To protect the linear actuator 60 from exposure to fluids within the wash chamber 13, a splash guard 64 may surround the portion of the linear actuator 60 that is within the wash chamber 13. In the illustrated embodiment, the splash guard 64 comprises a square tube with a lower end that is affixed to the spacer top plate 48 (using any suitable method of affixation (such as welding) that prevents or limits fluid from reaching the linear actuator 60) and that projects upward through an opening 66 defined in the top surface of the housing 12. As seen in FIGS. 3 and 4, the splash guard 64 raises and lowers in conjunction with the fluid manifold 40 and the spacer 46. In this embodiment, a wiper gasket or the like (not illustrated) provides a fluid seal between the opening defined in the top surface of the housing 12 and the outer surface of the splash guard 64.

The lowermost panel of the sidewall 16 may include a drain 72, leading to a valve 74, which in turn leads to a hose or the like (not illustrated) for removing fluid from the device 10 as needed during and/or after a wash cycle. This drain may be positioned anywhere on the bottom face of the wash compartment and use any suitable geometry such that the drain hole is at the lowest point of the compartment and gravity causes fluids to move to the drain.

The housing 12 may include one or more UV transparent windows 78 to enable UV light from a UV light fixture 80 to enter the wash chamber 13 and to shine upon one or more of the well plates therein and/or one or more of the internal surfaces for sanitization purposes. The UV light fixture preferably emits UV-C light at a wavelength of 254 nm. In the illustrated embodiment, there are two opposing UV transparent windows 78 such that UV light shines directly on the well plates in the opposing side positions (position B and position D in FIG. 2). Although not illustrated, the UV light fixtures 80 will typically have a cover to block the UV light from shining anywhere except toward and through the UV transparent windows 78. This cover may be comprised of a preferably semi-cylindrical mirror to reflect light towards the window and plates. Some or all of the inner surfaces of the housing 12 may be UV-reflective (either inherently or due to an applied coating) to increase the dispersion of the UV light throughout the wash chamber 13.

One or more ultrasonic transducers 76 (four are illustrated) may be affixed to the housing 12 to impart an ultrasonic vibration to fluid pooling in the wash chamber 13 as desired during a wash cycle to assist in cleaning the well plates. In one exemplary embodiment, the ultrasonic transducers vibrate at 40 kHz. As illustrated, it may be desirable to affix the ultrasonic transducers to the bottom or lower portion of the housing, directed upward, as the bottom or lower portion of the housing will be in contact with the pooled fluid (the wash chamber 13 will typically only be partially filled with fluid, if at all) such that the illustrated location of the ultrasonic transducers will more efficiently impart an ultrasonic vibration to the pooled fluid. The ultrasonic vibration imparted to the pooled fluid creates a sonication bath via cavitation bubbles. The vibration and cavitation bubbles aid in cleaning a well plate that is submerged in the fluid. Other embodiments of the device may introduce ultrasonic waves through alternative modes, such as probes going directly into the cavities of the well plates in the top rotor position.

One or more fluid spray nozzles 70 may be positioned within the wash chamber 13 (two nozzles are illustrated in the figures). The spray nozzles 70 are used to introduce fluid into the wash chamber 13. The fluid introduced into the wash chamber 13 may be, for example, deionized (DI) water or a cleaning solution. One or more pumps 98 may be used to pump the fluid to the spray nozzles 70 from a reservoir (not illustrated) via hoses or pipes (not illustrated). The spray nozzle 70 may introduce fluid into the wash chamber 13 for at least two different reasons. First, the fluid may be introduced into the wash chamber 13 to at least partially fill the wash chamber 13 to be able to submerge at least the well plate in the bottom position (position C in FIG. 2) in the fluid as part of the wash cycle (optionally, the wash chamber 13 may be filled with enough fluid to submerge the well plates in three positions (the left, right, and bottom positions), all four positions, or two positions in an orientation where the rotor is rotated 45° from what is displayed in FIG. 2). Second, the spray nozzle 70 may enable the sprayed fluid to reach some or all of the internal surfaces of the wash chamber 13, thereby helping to clean those surfaces of any debris. In one embodiment, the nozzles may be 360° spray nozzles in order to spray fluid in a pattern that will allow for a single or more nozzles to clean all internal compartment and rotor surfaces. In alternative embodiments of the invention, a combination of tubing or nozzles may be positioned along the upper edges or faces of the compartment and direct fluid such that it flows down the inner walls of the wash compartment in a "waterfall" fashion.

It may be desirable that the device can conduct a self-clean operation of the wash chamber 20 and components within the wash chamber 20, in order to remove contaminants that may be introduced to the wash chamber 20 during a wash process and sanitize the space. To conduct a self-clean, the bath can be filled with reagent to a depth level such that the rotor 20 or parts mounted to the rotor are in contact with the reagent bath. The rotor 20 will then spin at high speed (typically 10-1000 rpm) in either or both directions, or in more complex movement patterns. When the rotor 20 or parts mounted to it collide with the reagent bath, it will forcibly splash and disperse the reagent throughout the wash chamber 13. A scoop (not illustrated) mounted to the rotor 20 may also be used to increase the volume and splash intensity of reagent that is displaced during this self-clean spin cycle. The UVC light (preferably 254 nm wavelength) from UV bulbs 80 may also be reflected and dispersed throughout the wash chamber 20 to sanitize the space.

The device 10 may comprise one or more heaters 100 to heat the air inside the wash chamber 13 for drying and/or disinfecting purposes. In one embodiment of the invention, a heating unit is mounted directly to the outer surface of the metal housing 12 to heat the housing 12. The air inside the wash chamber 13 will then be heated via conduction with the housing 12. In other embodiments of the invention, air will be heated external to the wash compartment and then be pumped into the compartment through any suitable pump, such as a blower or fan 102.

Figure 11:
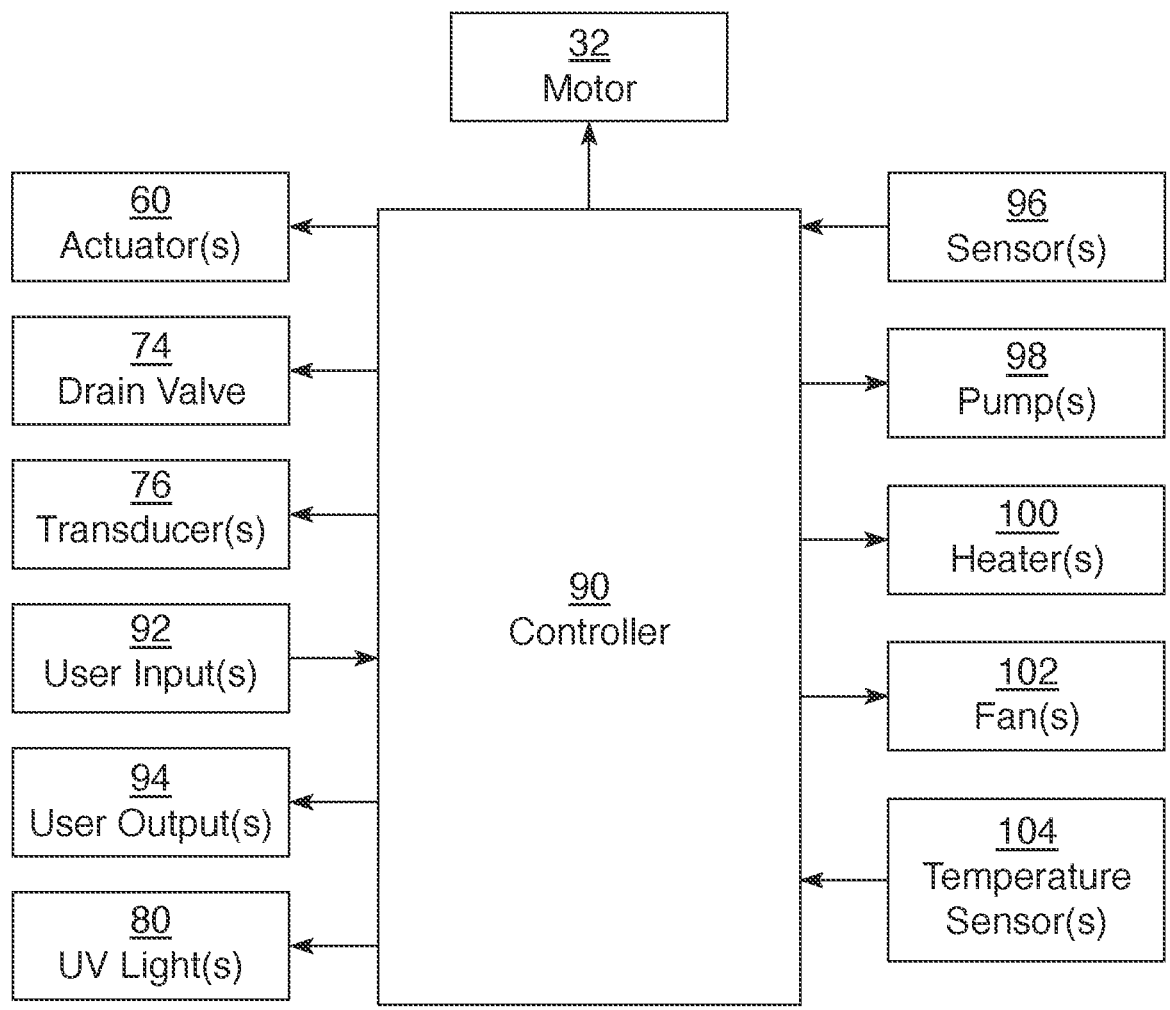
FIG. 11 illustrates a control system of a well plate washing device, in accordance with embodiments of the invention.

Referring now to FIG. 11, a control system of a well plate washing device is illustrated in accordance with embodiments of the invention. The well plate washing device 10 comprises a controller 90. The controller 90 may comprise a microprocessor, dedicated or general purpose circuitry (such as an application-specific integrated circuit or a field-programmable gate array), a suitably programmed computing device, or any other suitable means for controlling the operation of the device 10. The controller 90 may receive inputs from one or more user inputs devices 92, such as buttons, switches, knobs, keypad, bar code reader, magnetic scanner, RFID scanner, etc. This embodiment of the invention will primarily use a touchscreen LCD for user inputs. The controller 90 may provide outputs to one or more user output devices 94, such as lights, LED or LCD displays, sound generators (such as buzzers or beepers), etc. The controller 90 may receive inputs from one or more sensors 96, such as described above. The controller 90 may receive inputs from one or more temperature sensors 104. The controller 90 may control the extension and retraction of the linear actuator 60 and additional actuators in other embodiments. The controller 90 may control the opening and closing of the drain valve 74. The controller 90 may turn on and off one or more of the ultrasonic transducers 76, the pumps 98, the UV lights 80, heaters 100, and/or fans 102. As described above, the controller may control the motor and its movement patterns.

The well plate washing device of embodiments of the invention may be adapted to perform many different wash routines comprising many different steps in any suitable order. Some exemplary wash routines/steps are described herein for illustrative purposes but are not intended to be limiting. A high level workflow using a well plate washing device of embodiments of the invention may comprise the following steps: conducting an experiment/reaction using one or more new or cleaned well plates; transferring up to four used well plates into the well plate washing device, cleaning the well plate(s) of any experiment/reaction chemicals using one or more of the steps described herein, removing the clean well plate(s) from the device, and using the clean well plate(s) in a new experiment/reaction. These steps may be repeated as needed.

Any suitable cleaning fluid or reagent (these terms are used interchangeably herein) may be used in the well plate washing device of embodiments of the invention, such as GrenoClean from Grenova, Inc., ethanol, DI water, bleach, etc. (and combinations thereof). The cleaning fluid or reagent is used to chemically break down and sanitize experiment residues.

The well plate washing device of embodiments of the invention may use any or all of the following actions/techniques, in any order, in the cleaning process: pressure jet spray, centrifugal spin, dry, rotary agitation, ultraviolet light, and/or sonication. A pressure jet spray results when a cleaning fluid or reagent is sprayed into the top openings of the well plate in the top position via the fluid manifold. The sprayed reagents will mechanically disrupt residue at the bottom of the cavities. After the pressure jet spray, the rotor assembly will spin at a high rpm (typically 100-1000 rpm) in order to eject fluids and contaminants (mixed with reagents) from inside of cavities via centrifugal force. At the end of a wash procedure, the rotor assembly will typically spin at a high rpm (typically 100-1000 rpm) in order to dry the plate cavities of remaining fluids via centrifugal force. The speed and acceleration/deceleration profiles of the spins may vary and depend on the objects and residues being washed. To provide rotary agitation, the rotor will alternate rotating clockwise and counterclockwise in quick succession with the wash chamber filled to a high enough level that the well plate in the bottom position moves back and forth in a reagent bath. This rotary agitation causes reagent to move around inside of the cavities to mechanically disrupt residue. This rotary agitation may use different speeds, angles, and frequencies and movement profiles. For example, if you consider a plate pointing straight down as 0° position, then rotary agitation may occur by rotating the rotor from −40° to 40° and back to −40° at a speed of 60 rpm and frequency of 4 Hz. The degree of back-and-forth motion may be sufficient to cause the well plate to repeatedly exit and reenter the reagent bath to create a "hard splash." Alternatively, the rotor may spin multiple complete rotations in one direction to repeatedly splash all of the well plates through the reagent bath. While one plate is in the reagent bath, the well plates in at least the left and right positions may be exposed to UV-C light (e.g., at a wavelength of 254 nm) to sanitize the well plates and break down biomolecules in the well plate cavities. To provide sonication, at least the well plate in the bottom position is submerged in a reagent bath and the ultrasonic transducers are activated thereby producing sonication which cause cavitation in the fluid inside of inverted cavities. Cavitation will attack and destroy residue on the well plate.

In order to maximize the effectiveness of a sonication bath, plate cavities should not contain any air bubbles or pockets. This embodiment of the invention may use the manifold and fluid pump to fill the plate cavities with water or reagent prior to sonicating the plate. Once the plate cavities are full of fluid, the rotor will be rotated 180°, such that the filled plate goes to the bottom position for sonication in the reagent bath. A combination of surface tension, capillary action, and pressure barriers will generally keep fluid contained within the plate cavities, even as the cavities are turned upside down. Additionally, this embodiment of the invention may use rotary agitation in order to minimize air pockets in wells. When a plate is submerged in the reagent bath, rotary agitation will cause bath fluid to splash and flow into the plate cavities. When a bath fluid enters the cavities during agitation, it forces out air that was present in the cavities. The speed, angle, frequency, water level, and travel pattern of rotary agitation intended to explicitly remove air pockets may be different than the parameters for rotary agitation intended to clean the plate.

A specific exemplary cleaning cycle will now be described in more detail. The well plates are loaded into the device one at a time, either manually or automatically. In the illustrated embodiment, as few as one or as many as four well plates may be loaded. One well plate is loaded through the front panel opening 15 onto the plate holder 24 in the top position. If more than one well plate is to be loaded, the rotor 20 is rotated 90° (or 180° if only loading two well plates) so that the next well plate can be loaded into the next plate holder 24. The loading process is repeated until all of the well plates are loaded. The door or cover (not illustrated) is closed to cover the front panel opening 15.

A pump 98 is activated to pump reagent to the fluid manifold 40 to spray the reagent into the cavities of the well plate, thereby performing a pressure jet spray of the well plate in the top position. In one embodiment, reagent is sprayed for approximately 1.5 seconds at each well plate. If more than one well plate was loaded, the rotor 20 is rotated 90° (or 180° if only two well plates were loaded) and the reagent is then sprayed from the fluid manifold 40 into the cavities of the well plate that has just been moved into the top position. This rotation and pressure jet spray are repeated until all of the well plates have been sprayed with the reagent. A rinsing fluid (such as deionized water) may also be sprayed at each well plate, either immediately after each well plate is sprayed with reagent or after all of the well plates have been sprayed with reagent. The manifold may also be used to shoot pressurized air into the plate cavities. The rotor 20 is then rotated at a high rpm (approximately 400 rpm in one embodiment) for a specified amount of time (approximately 5 seconds in one embodiment) such that centrifugal force ejects reagent and residue from all of the well plates. The pressure jet spray and spin cycle may be repeated any number of times as desired.

Optionally, before or typically after the pressure jet spray of all well plates and the spin cycle, the wash chamber 13 may be filled with enough reagent to submerge at least the well plate in the bottom position. The reagent is sprayed from the spray nozzles 70 (or other fill ports in other embodiments) which may simultaneously fill the wash chamber and clean the walls of the wash chamber, the fluid manifold, and other internal structures. After the wash chamber 13 is filled with the desired amount of reagent, reagent may be sprayed (typically at a lower pressure than used in the pressure jet spray) into the cavities of the well plate in the top position and the rotor 20 is rotated 180° to submerge this well plate in the reagent bath. This pre-filling of the cavities of the well plate prior to submersion reduces air bubbles in the cavities of the inverted well plate. The ultrasonic transducers may then be activated to produce cavitation in the reagent bath which will attack residue in the cavities and on the walls of the well plate. While the well plate is in the reagent bath, rotary agitation as described above may be used to slosh reagent around the well plate and inside the cavities of the well plate. The rotor 20 is rotated 90° (or 180° if only two well plates were loaded) and this cycle is repeated for the remaining well plates. Any fluid in the wash chamber, such as fluid from the pressure jet spray and or the reagent bath, may be drained by opening the drain valve 74 and/or activating a drain pump (not illustrated). After the reagent bath fluid has been drained, the rotor 20 is typically spun at a high rpm (800 rpm in this embodiment) in order to eject any remaining fluid in the cavities of the well plates to dry the well plates. Optionally, air (heated or not) may be pumped into the wash chamber 13 to help dry the well plates.

While the well plate in the top position is being pressure sprayed and the well plate in the bottom position is in the reagent bath, the well plates in the left and right positions may be receiving UV-C light from the UV lights 80 on opposite sides of the wash chamber 13.

In the illustrated embodiment of the invention, a wash cycle (such as any of the ones described herein) may be completed with as few as one well plate loaded in the device. In the illustrated embodiment, most or all of the wash cycle steps described herein would typically not be performed simultaneously on one specific well plate. For example, a UV-C light treatment would typically not be performed on a well plate at the same time as a pressure sprayed or sonication bath is being performed on the same well plate. However, in other embodiments of the device with different spatial arrangements or methods of cleaning step applications, multiple different wash processes may occur to a single plate simultaneously.

Multiple different fluid reservoirs (not illustrated) and multiple different supply lines (not illustrated) may be used to supply a plurality of different cleaning fluids to the fluid manifold of the device. For example, there may be four different fluid reservoirs containing, respectively, deionized water and three different reagents.

The valves, actuators, and pumps may be powered using compressed air. As such, an air compressor and/or compressed air tank (not illustrated) may supply compressed air to the device using air supply lines (not illustrated). Alternatively, these components and other moving components may be powered electronically.

As described above, fluid is pressure sprayed into the cavities of the well plates via the fluid manifold. In one embodiment of the invention, a fluid pump fills a supply line to the fluid manifold with a reagent, and then a valve is activated to release compressed air into the line and force reagent through the wash manifold at a higher pressure than would be supplied by the fluid pump. The same mechanism may be used to fill the wash compartment bath and clean the compartment by using a three-port diverter valve or the like to switch the fluid flow from the fluid manifold supply line to the supply line(s) leading to the spray valve(s).

The fundamental technology of the cleaning device presented in this description is based on the concept of using rotational movement in order to transport an object to multiple different cleaning process steps, when the different cleaning processes cannot be conveniently conducted from the same location or orientation. Using pipette tips and well plates as an example: to wash pipette tips with these cleaning methods—a device can direct a pressure jet spray from the top opening of the tips and sonicated fluid from below through the bottom openings of the tips; however, to wash well plates—since the bottoms are closed off, both pressure jet sprays and sonication must be directed into the top openings of the cavities. Therefore, using a rotor to move well plates to different locations and orientations allow for additional wash methods (that need to be directed from the same direction—specifically into the cavities, perpendicular to the plates' top faces) to be applied to the plates in a single wash process. This same methodology and concept may be applied to numerous different objects in numerous different industries and contexts.

The fundamental technology of using rotational movement to transport objects to multiple cleaning process steps also allows multiple well plates to be washed in parallel. Using the illustrated embodiment as an exemplar, the rotor with four positional mounts allows four plates to be cleaned simultaneously. Each plate can undergo a certain cleaning operation, while the adjacent and opposite plates undergo different cleaning operations in parallel. Subsequentially, each well plate can then be rotationally moved to a new position to undergo a different cleaning operation. This allows multiple to be cleaned at the same time. This, however, is not intended to be limiting, and the overall rotational transport concept can be applied to any number of different objects undergoing any number of different or same cleaning operations.

Using rotational transport allows for the objects to be rotated about a central axis at high speeds (typically 100-1000 rpm) in order to eject contaminants and fluids off of the surfaces or inner cavities of the objects. This serves as both a cleaning operation and a drying operation for the objects.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below (if any) are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

That which is claimed:

1. A device for cleaning one or more items, each item to be cleaned defining a plurality of cavities, the device comprising:
   an enclosure defining a wash chamber, the enclosure including a side wall, a rear wall, and a front panel;
   at least one fluid spray nozzle within the wash chamber to at least partially fill the wash chamber with cleaning fluid, to spray an internal surface of the wash chamber, and to create a reservoir of cleaning fluid such that each item to be cleaned is fully submerged in cleaning fluid;
   a drain in a lowest point of the wash chamber allowing cleaning fluid to be drained from the wash chamber;
   a rotor positioned within the wash chamber and selectively rotatable about an axle, the rotor comprising a plurality of holders spaced about the axle, each holder adapted to selectively receive and hold a respective item to be cleaned such that the cavities of each item to be cleaned are facing away from the axle, the rotor being selectively rotatable into and stoppable at each of a plurality of different orientations, the number of different orientations being equal to or greater than the number of holders such that each of the plurality of holders is in a respective different position when the rotor is in each of the plurality of different orientations;

a motor for selectively rotating the axle and thereby selectively rotating the rotor;

a fluid manifold dispenser comprising at least one liquid input and at least one liquid output, the fluid manifold dispenser positioned such that the at least one liquid output is adapted to operably direct cleaning fluid to contact a different one of the items to be cleaned to clean material out of the cavities when the rotor is in a respective different orientation and the one or more items to be cleaned are held by their respective holder, the fluid manifold dispenser with the at least one liquid output is raised vertically relative to the rotor to a position in which the fluid manifold dispenser does not obstruct the selective rotation of the rotor and the fluid manifold dispenser is lowered vertically relative to the rotor to a position in which the fluid manifold dispenser is positioned a predefined distance apart from the item to be cleaned at which the at least one liquid output of the fluid manifold dispenser is to operably direct the cleaning fluid, wherein the enclosure includes an opening in a top surface of the side wall within which the fluid manifold dispenser moves and a linear actuator raising and lowering the fluid manifold relative to the opening in the top surface of the side wall to move the at least one liquid output of the fluid manifold toward and away from the item to be clean; and wherein the rotor is selectively rotatable at a predefined rotational speed for a predefined amount of time, such that the rotation of the rotor is adapted to expel the cleaning fluid operably directed by the dispenser from the cavities of each item to be cleaned.

2. The device of claim 1, wherein the fluid manifold dispenser comprising at least one liquid input and a plurality of liquid outputs.

3. The device of claim 2, wherein a number of liquid outputs of the fluid manifold dispenser is equal to a number of cavities of each item to be cleaned such that each one of the fluid outputs operably directs fluid at a corresponding one of the cavities.

4. The device of claim 1, wherein each item to be cleaned is fully submerged in cleaning fluid at least once during each complete rotation of the rotor.

5. The device of claim 4, wherein the rotor is selectively rotatable back-and-forth such that the rotor is adapted to move a fully submerged item to be cleaned back-and-forth within or repeatedly in-and-out of the reservoir of cleaning fluid.

6. The device of claim 4, further comprising one or more transducers capable of outputting sound in an ultrasonic range into the wash chamber and into the reservoir of cleaning fluid.

7. The device of claim 1, further comprising one or more ultraviolet (UV) lights positioned to emit UV light into the wash chamber and at one or more items to be cleaned.

8. The device of claim 1, wherein the one or more items to be cleaned comprise one or more pieces of laboratory equipment.

9. The device of claim 8, wherein the one or more pieces of laboratory equipment comprise one or more well plates.

* * * * *